United States Patent [19]

Parker

[11] 4,011,333
[45] Mar. 8, 1977

[54] SUBSTITUTED THIOPHENECARBOXYLIC ACID AND ESTERS AS HYPOLIPIDEMIC AGENTS

[75] Inventor: Roger Alan Parker, Cincinnati, Ohio

[73] Assignee: Richardson-Merrell Inc., Wilton, Conn.

[22] Filed: June 16, 1975

[21] Appl. No.: 587,045

[52] U.S. Cl. .................. 424/275; 260/332.2 C; 260/332.3 R; 424/361
[51] Int. Cl.² .................................. A61K 31/38
[58] Field of Search ............ 260/332.2 C, 332.3 R; 424/275

[56] References Cited
UNITED STATES PATENTS

| | | | |
|---|---|---|---|
| 2,462,697 | 2/1949 | Weinmayr | 260/332.2 C |
| 3,360,527 | 12/1967 | Naito et al. | 260/306.7 C |

*Primary Examiner*—Albert T. Meyers
*Assistant Examiner*—Vera C. Clarke
*Attorney, Agent, or Firm*—L. Ruth Hattan; Eugene O. Retter; George W. Rauchfuss, Jr.

[57] ABSTRACT

Substituted thiophenecarboxylic acid and esters and pharmaceutically acceptable salts thereof of the following general structure are useful as hypolipidemic agents:

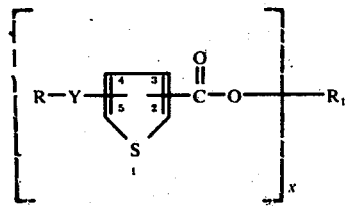

wherein Y is selected from oxygen and divalent sulfur; R is selected from a straight or branched saturated hydrocarbon chain of from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl group of from 1 to 6 carbon atoms, benzyl, phenethyl, alkane-poly-yl containing from 3 to 6 carbon atoms, and 1,2,3,4,5,6-cyclohexanehexayl; X is an integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1.

20 Claims, No Drawings

SUBSTITUTED THIOPHENECARBOXYLIC ACID AND ESTERS AS HYPOLIPIDEMIC AGENTS

FIELD OF INVENTION

This invention relates to the use of substituted thiophenecarboxylic acids, esters, and pharmaceutically acceptable salts thereof as hypolipidemic agents and compositions comprising said compounds.

DESCRIPTION OF PRIOR ART

E. Profft in Montasber. Deut. Akad. Wiss. Berlin 1, 180–8 (1959) suggests the preparation of 5-n-dodecylthiothiophene-2-carboxylic acid and 5-n-octadecylthiothiophene-2-carboxylic acid, but discloses no utility for the compounds. To applicant's knowledge the use of the compounds described herein as hypolipidemic agents has not been described heretofore.

SUMMARY OF INVENTION

Compounds of the following general Formula I are useful as hypolipidemic agents:

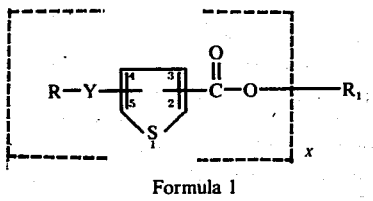

Formula I wherein Y is selected from oxygen and divalent sulfur; R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl group of from 1 to 6 carbon atoms, benzyl, phenethyl, alkane-poly-yl containing from 3 to 6 carbon atoms and from 2 to 6 univalent bonds, and 1,2,3,4,5,6-cyclohexanehexayl; X is an integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1.

Pharmaceutically acceptable salts of compounds of general Formula I wherein $R_1$ represents hydrogen are also included within the scope of this invention.

DETAILED DESCRIPTION OF INVENTION

In the above general Formula I, the substituent group represented by R-Y- and the acid function may be attached at any of the positions 2-, 3-, 4-, or 5- of the thiophene ring with the proviso that the acid function and the group R-Y- are not attached to the same carbon atoms.

R may be a straight or branched saturated hydrocarbon chain of from 10 to 20 carbon atoms in which case the substituent group R-Y- may be represented as $C_nH_{2n+1}Y$- wherein Y is oxygen or divalent sulfur, and n is an integer of from 10 to 20, and the hydrocarbon chain may be straight or branched.

R may also be a straight or branched unsaturated hydrocarbon chain of from 10 to 20 carbon atoms containing from 1 to 4 double bonds in which case the substituent group R-Y- may be represented as $C_nH_{2n-m}Y$- wherein Y is oxygen or divalent sulfur, n is an integer of from 10 to 20, and m is the integer 1, 3, 5 or 7 to give either one, two, three or four double bonds in the hydrocarbon chain which may be straight or branched.

Illustrative examples of straight or branched saturated hydrocarbon chains which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, 3-methyloctadecyl, nonadecyl and didecyl. Illustrative examples of a straight or branched unsaturated hydrocarbon chains containing from 1 to 4 double bonds which R may represent are, for example, 10-undecenyl, 9,12-octadecadienyl, 3,7,11-trimethyl-2,6,10-octatrienyl, 3,7-dimethyl-2,6-octadienyl, 5,9-dimethyl-2,4,8-decatrienyl, 3,7-dimethyloct-6-enyl, 1,2,5,9-tetramethyl-2,4,8-decatrienyl and 11-didecenyl. Both the cis- and trans- isomers of the unsaturated hydrocarbon chain are included within the scope of this invention.

Illustrative examples of straight or branched lower alkyl groups which $R_1$ may represent in general Formula I are, for example, methyl, ethyl, n-propyl, isopropyl, n-butyl, tert-butyl, pentyl and hexyl.

The group alkane-poly-yl contains from 3 to 6 carbon atoms and from 2 to 6 univalent bonds. Illustrative examples of alkane-poly-yl groups which $R_1$ may represent in the above general Formula I are, for example, 1,3-propanediyl, 1,2,3-propanetriyl, 1,2-propanediyl, 1,2,3,4,5,6-hexanehexayl, 1,5-pentanediyl and 1,6-hexanediyl.

The term 1,2,3,4,5,6-cyclohexanehexayl is taken to mean a cyclohexane radical with a univalent bond extending from each of the 6 carbon atoms.

Pharmaceutically acceptable salts of the compounds of general Formula I wherein $R_1$ represents hydrogen are those formed with any suitable inorganic or organic basis such as those of alkali metals, for example, sodium and potassium; alkaline earth metals, for example, calcium and magnesium, light metals of Group III A, for example, aluminum; organic amines, such as primary, secondary, or tertiary amines, for example, cyclohexylamine, ethylamine, and piperidine. The salts can be prepared by conventional means, such as, by contacting and neutralizing a solution of a compound of Formula I having a carboxylic acid group in a polar solvent with the stoichiometric quantity of a base, for example, sodium hydroxide.

It is apparent from the above general Formula I that wherein $R_1$ is other than alkane-poly-yl or 1,2,3,4,5,6-cyclohexanehexayl the compounds are alkoxy- or alkylthio- thiophenecarboxylic acid or mono- ester derivatives or salts as represented by the following general Formula II, or when $R_1$ is alkane-poly-yl or 1,2,3,4,5,6-cyclohexanehexayl the compounds are polyester derivatives of alkoxy- or alkylthiothiophenecarboxylic acid as represented by the following general Formula III.

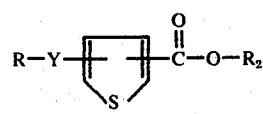

Formula II

In the above general Formula II, Y represents oxygen or divalent sulfur; R represents a straight or branched saturated hydrocarbon chain containing from 10 to 20 carbon atoms or a straight or branched unsaturated hydrocarbon chain containing from 10 to 20 carbon atoms and from 1 to 4 double bonds; $R_2$ represents hydrogen, a straight or branched lower alkyl group of from 1 to 6 carbon atoms, such as, for example, methyl, ethyl, n-propyl, isopropyl, tert-butyl, and pentyl; benzyl and phenethyl.

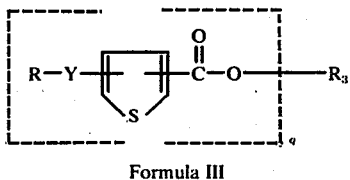

Formula III

In the above general Formula III, Y represents oxygen or divalent sulfur; R represents a straight or branched saturated hydrocarbon chain containing from 10 to 20 carbon atoms or a straight or branched unsaturated hydrocarbon chain containing from 10 to 20 carbon atoms and from 1 to 4 double bonds; $R_3$ represents alkane-poly-yl containing from 3 to 6 carbon atoms and from 2 to 6 univalent bonds, or 1,2,3,4,5,6-cyclohexanehexayl; and $q$ is an integer of from 2 to 6.

The use of the compounds represented by each of Formulas II and III as hypolipidemic agents represents a preferred embodiment of this invention. A more preferred embodiment of this invention is the use of the compounds as represented by general Formula II as hypolipidemic agents. Within this more preferred embodiment, the use as hypolipidemic agents of the compounds of general Formula II wherein the R-Y- substituent is attached to the 5-position of the thiophene ring, and the acid function is attached to the 2-position of the thiophene ring as illustrated in the following general Formula IV represents an even more preferred embodiment of this invention.

Formula IV

In the above general Formula IV the substituent groups R and Y have the meanings defined in general Formula I, and the substituent group $R_2$ has the meaning defined in general Formula II. The use as hypolipidemic agents of the benzyl ester of the compounds of general Formula IV, that is, compounds of general Formula IV wherein $R_2$ represents benzyl, represents a particularly preferred embodiment of this invention.

Illustrative examples of compounds of this invention are, for example, 5-decyloxy-2-thiophenecarboxylic acid, 5-tetradecyloxy-2-thiophenecarboxylic acid, 5-(trans-9-octadecenyloxy)-2-thiophenecarboxylic acid, 5-dodecyloxy-2-thiophenecarboxylic acid, 5-tetradecyloxy-2-thiophenecarboxylic acid methyl ester, 5-tetradecyloxy-2-thiophenecarboxylic acid ethyl ester, 5-octadecyloxy-2-thiophenecarboxylic acid, 5-tetradecylthio-2-thiophenecarboxylic acid, 4-dodecylthio-2-thiophenecarboxylic acid butyl ester, 3-tridecyloxy-2-thiophenecarboxylic acid benzyl ester, 5-hexadecyloxy-2-thiophenecarboxylic acid methyl ester, 2-heptadecyloxy-3-thiophenecarboxylic acid, 4-undecylthio-3-thiophenecarboxylic acid ethyl ester, 5-hexadecyloxy-2-thiophenecarboxylic acid ethyl ester, 5-pentadecylthio-2-thiophenecarboxylic acid phenethyl ester, 5-tetradecyloxy-2-thiophenecarboxylic acid diester with 1,3-propanediol, 5-hexadecyloxy-2-thiophenecarboxylic acid hexaester with inositol, 4-decyloxy-2-thiophenecarboxylic acid triester with glycerol, 5-undecyloxy-2-thiophenecarboxylic acid ethyl ester, 5-nonadecyloxy-2-thiophenecarboxylic acid phenethyl ester, 5-didecyloxy-2-thiophenecarboxylic acid propyl ester, 3-didecyloxy-2-thiophenecarboxylic acid hexylester, 5-(10-undecenyloxy)-2-thiophenecarboxylic acid, 4-(trans-trans-1,2,5,9-tetramethyl-2,4,8-decatrienyloxy-2-thiophenecarboxylic acid ethyl ester, 5-(cis-cis-9,12-octadienyloxy)-3-thiophenecarboxylic acid benzyl ester, and 5-(3,7-dimethyloct-6-enyloxy)-2-thiophenecarboxylic acid.

The compounds described herein are useful as hypolipidemic agents in that they reduce blood lipids, particularly cholesterol and triglycerides without concurrent accumulation of desmosterol. These compounds can be administered to animals, mammals, rats, cats, dogs, cattle, horses and humans and can be useful in the treatment of hyperlipidemic states such as are encountered in patients with cardiovascular diseases that can result in heart failure and stroke. As used herein, the term patient is intended to mean the animal or mammal being treated.

To illustrate the utility of the compounds disclosed herein, young male rats of the Wistar strain initially weighing about 175 grams were given free access to a diet which contained 0.15% by weight of test compound, that is, a compound of general Formula I. This diet was prepared by mixing the test compound with commercial Purina Chow. (Trademark of Ralston-Purina Co., St. Louis, Mo.). Groups of animals were given these diets for either 4 or 10 days. Control groups of 6 rats each were given Purina Chow to which no test compounds had been added. At the end of the treatment period all rats were bled by cardiac puncture, and the plasma was analyzed for cholesterol and triglyceride content. The results are given in the following Table I.

Table 1

| Test Compound: | 5-(tetradecylthio)-2-thiophenecarboxylic acid | 5-(tetradecyloxy)-2-thiophenecarboxylic acid |
|---|---|---|
| Duration of Treatment (Days) | 4 | 4 |
| Daily Dose: mg/kg (a) | 165 | 165 |
| No. Rats | 6 | 6 |
| Plasma Cholesterol % Reduction (b) | 15 | 54 |
| Plasma Triglycerides % Reduction (b) | 61 | 83 |

(a) Determined by measuring food consumption.
(b) Compared to untreated control rats in the same experiment.

The compounds of this invention can be administered orally or parenterally either alone or in the form of pharmaceutical preparations. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any lipid lowering effective amount. The quantity of compound administered can vary over a wide range to provide from about 0.5 mg/kg (milligram per kilogram) to about 300 mg/kg of body weight of the patient per day, and preferably, from about 10 mg/kg to 30 mg/kg of body weight of the patient per day, to achieve the desired effect. Unit doses can contain from about 50 mg to 1 g (gram) of a compound of this invention and may be administered, for example, from 1 to 4 times daily.

The compounds of general Formula I wherein $R_1$ is hydrogen are prepared by aromatic nucleophylic substitution [J. March, *Advanced Organic Chemistry: Reactions, Mechanisms, and Structure*, MacGraw-Hill, p. 500 (1968)] as outlined below.

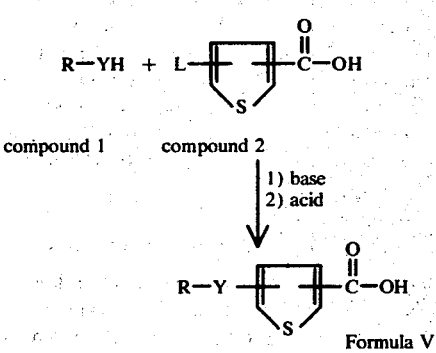

In the above general reaction Y represents oxygen or divalent sulfur; R represents a straight or branched saturated hydrocarbon chain containing from 10 to 20 carbon atoms or a straight or branched unsaturated hydrocarbon chain containing from 10 to 20 carbon atoms and from 1 to 4 double bonds; L represents a leaving group such as nitro, fluoro, chloro, bromo, or iodo, the preferred leaving group being chloro. The substituent group L on compound 2 and R-Y- on compounds of Formula V and the

group may be attached at the 2-, 3-, 4-, or 5-position of the thiophene ring, with the proviso that both L or R-Y- and

are not attached to the same position of the thiophene ring.

The above reaction may be carried out with or without a solvent. Suitable solvents for the reaction include benzene, xylene, toluene, chlorinated aromatic hydrocarbons, such as, chlorobenzene, ethers, such as, bis(2-methoxyethyl)ether, 1,2-dimethoxyethane or anisole, dimethylformamide, dimethylacetamide, 1-methyl-2-pyrrolidone or pyridine. Preferred solvents are xylene and dimethylacetamide. Copper metal or a salt such as cuprous chloride may be optionally added to the reaction. Suitable basis for the reaction include sodium or potassium metal, sodium hydride, potassium amide, potassium tert-butylate or other strong bases, such as, potassium carbonate, potassium hydroxide, sodium hydroxide, and sodium carbonate. The temperature of the reaction varies from about room temperature that is, about 25° C, to reflux temperature of the solvents, and the reaction time varies from about 1 hour to about 7 days, and following completion of the reaction the carboxylate salt derivative is treated with a mineral or organic acid to give compounds of Formula V.

Alcohols as represented by compound 1 which find use in the above general reaction are commercially available or may be prepared by reductions of the corresponding carboxylic acid or aldehyde. The thiophenecarboxylic acid derivatives as represented by compound 2 may be prepared by several methods as described in the *Chemistry of Heterocyclic Compounds, Thiophene and Its Derivatives*, by H. D. Hartough, Interscience Publishers, Inc., N.Y., pp. 379–381 (1952).

The compounds of general Formula I wherein $R_1$ is hydrogen, and the substituent group R-Y- is attached at the 5-position of the thiophene ring, and the acid function is attached to the 2-position of the thiophene ring may also be prepared from the corresponding R-Y- substituted thiophenecarboxaldehyde by the Cannizzaro reaction as generally described by E. Profft, Monatsber. Deut. Acad. 1, 180–8 (1959), or by oxidation of the aldehyde with silver oxide or alkaline permanganate solution as generally described by H. D. Hartough, cited hereinabove, page 369.

The R-Y- substituted thiophenecarboxaldehydes employed in the above described alternate synthesis are obtained by treating an appropriate R-Y- substituted thiophene derivative with N-methylformanilide and phosphorus oxychloride followed by water hydrolysis as generally described, for example, in Fieser and Fieser Advanced Organic Chemistry, Reinhold Publishing Corporation, New York (1961).

The R-Y- substituted thiophene derivatives wherein Y represents sulfur can be obtained in the manner described by E. Profft, Chemiker-Zeitung, 82, 298 (1958) and wherein Y represents oxygen can be prepared from the 3-thiolen-2-one (R. T. Hawkins, Journal Heterocyclic Chemistry, 11, (3) 291–4 (1974)) with a suitable alkyl halide, alkyl mesylate or alkyl tosylate in the presence of a base, for example, sodium hydride, potassium amide, potassium tert-butylate, sodium or potassium metal, potassium carbonate, sodium carbonate, triethylamine, or pyridine to yield the 2-alkoxythiophene intermediates. This reaction may be carried out with or without the solvent. Suitable solvents include pyridine, benzene, xylene, chlorobenzene, ethers, for example, bis(2-methoxyethyl) ether or anisole, dimethylformamide, dimethylacetamide, and hexamethylphosphoric triamide. The alkyl halide may be, for example, alkyl chloride, alkyl bromide, or alkyl iodide. The alkyl moiety in the alkyl halide, the alkyl mesylate, or the alkyl tosylate is a hydrocarbon radical containing from 10 to 20 carbon atoms which may be straight or branched and which may be saturated or unsaturated in which case it may contain from 1 to 4 double bonds.

The compounds of general Formula I wherein $R_1$ is hydrogen, and the substituent group R-Y- is attached to the 5-position of the thiophene ring, and the acid function is attached to the 2-position of the thiophene ring may also be prepared by a Friedel-Crafts acylation of an appropriate R-Y- substituted thiophene derivative with acetyl halide, for example, acetyl chloride, or acetyl bromide, or acetic anhydride with an acid catalyst, for example, borontrifluoride-etherate, stannic chloride, zinc chloride, hydriodic acid or orthophosphoric acid with or without a solvent to give the corresponding 5-R-Y-2-acetyl-substituted thiophene derivative. Suitable solvents for this reaction include methylene chloride, nitromethane, and chlorobenzene. Haloform oxidation of the 5-R-Y-2-acetyl-substituted thiophene derivative with hypohalite, for example, lithium hypochlorite, sodium hypochlorite, or sodium hypobromite, and aqueous base, for example, sodium hydroxide or potassium hydroxide and subsequent acidification with for example hydrochloric acid, will give the desired 5-R-Y-substituted-2-thiophene carboxylic acid derivatives. The Friedel-Crafts acylation and the haloform oxidation reactions are generally described by H. D. Hartough, cited hereinabove, pages 321 and 364 respectively. Metalation of the 5-R-Y-substituted thiophene derivatives with for example, butyllithium, sodium metal, diethyl mercury, ethyl magnesium chloride, or sodium amalgam, followed by treatment with dry ice and subsequent acidification with for example, hydrochloric acid will also give the 5-R-Y-thiophene-2-carboxylic acid derivatives.

Esterification of the thiophenecarboxylic acid as represented by the above general Formula V to give compounds of general Formula I wherein $R_1$ is other than hydrogen may be carried out by several methods. For example, compounds of Formula V are converted to the metal salts, for example, sodium or potassium or an amine salt, for example, ammonium salt or triethyl ammonium salt and subsequently reacted with an alkyl halide of the formula halo-$R_1$ or an alkyl sulfate of the formula $R_1SO_4R_1$ or a sulfonate of the formula $R_1O$-$SOR_7$ wherein $R_1$ has the meaning defined in general Formula I except that $R_1$ is not hydrogen, and $R_7$ is lower alkyl of from 1 to 4 carbon atoms or substituted aryl, for example, tosyl. Esterification of compounds of general Formula V may also be carried out by alcoholysis of the substituted thiophenecarboxylic acid chloride, which is formed by reacting the acid with the thionyl chloride, or of the substituted thiophenecarboxylic acid imidozolide, which is formed by reacting the acid with N,N'-carbonyldiimidazole, with an alcohol of the formula $R_1$—OH wherein $R_1$ has the meaning defined in general Formula I except that $R_1$ is not hydrogen. Esterification may also be promoted by the reaction of a substituted thiophenecarboxylic acid compound of general Formula V with an alcohol of the formula $R_1$—OH wherein $R_1$ has the meaning defined in general Formula I, except that $R_1$ is not hydrogen and a dehydrating agent, for example, N,N'-dicyclohexylcarbodiimide.

The following specific examples are illustrative of the compounds, processes, and compositions described herein.

EXAMPLE 1

5-(Tetradecylthio)-2-Thiophenecarboxylic acid

A mixture of 18.6 g (0.090 mole) of 5-bromo-2-thiophenecarboxylic acid, 25.0 g (0.109 mole) of 1-tetradecanethiol and 500 ml of dried dimethyl acetamide is stirred at room temperature after which 10.8 g (0.200 mole) of sodium methoxide is added. The mixture is heated and the methanol formed is allowed to distill off. The mixture is refluxed for 24 hours after which the mixture is cooled and poured into a water-ice mixture, acidified with 10% aqueous hydrochloric acid, filtered, and the precipitate washed with water and dried. The solid obtained is crystallized from the methanol then recrystallized from hexane to give 5-(tetradecylthio)-2-thiophene carboxylic acid, M.P. 106°–108° C.

EXAMPLE 2

5-(Tetradecyloxy)-2-thiophenecarboxylic acid

A mixture of 21.4 g (0.100 mole) of 1-tetradecanol, 5.9 g (0.146 mole) of sodium hydride (59.5% in oil) and 300 ml of dried xylene is heated to reflux with stirring for 2 hours then allowed to cool after which 7.5 g (0.046 mole) of 5-chloro-2-thiophenecarboxylic acid is added. The mixture is refluxed for 64 hours after which the mixture is cooled and poured into a water-ice mixture, acidified with acetic acid, and extracted with the addition of ether. The ether is evaporated and aqueous layer extracted 5 times with water: strong ammonia solution (1:1). The combined aqueous extract is acidified with acetic acid. The solid obtained is crystallized twice from hexane to give 5-(tetradecyloxy)-2-thiophenecarboxylic acid, M.P. 95°–96° C.

EXAMPLE 3

5-(Hexadecyloxy)-2-thiophenecarboxylic acid

A mixture of 20 g (0.2 mole) of 3-thiolen-2-one [R. T. Hawkins, Journal Heterocyclic Chemistry, 11, (3), 291–4 (1974)], 61.1 g (0.2 mole) of 1-bromohexadecane, and 4.8 g (0.2 mole) of sodium hydride in dry benzene is refluxed with stirring for 24 hours after which the solvent is removed and the product distilled to give 2-hexadecyloxythiophene.

To a cooled mixture of 27 g of N-methylformanilide and 27 g (0.176 mole) of phosphorus oxychloride is added 32.5 g (0.1 mole) of 2-hexadecyloxythiophene. The mixture is warmed to 70° C under vacuum (10 mm Hg). The mixture is allowed to stand at 60°–70° C for 7 hours, then overnight at room temperature after which the mixture is stirred into 100 g of ice. The mixture is extracted into benzene, washed with water, dried over sodium sulfate and distilled in vacuo to give 5-hexadecyloxy-2-thiophenecarboxaldehyde. The carboxaldehyde (7.1 g, 0.02 mole) is stirred vigorously with 4 g of potassium hydroxide in 2.6 ml of water for 24 hours. The mixture is diluted with water and extracted into ether. The aqueous layer is separated and acidified with hydrochloric acid precipitating 5-(hexadecyloxy)-2-thiophenecarboxylic acid.

EXAMPLE 4

5-(Cis-9-octadecenyloxy)-2-thiophenecarboxylic acid

When in Example 2 oleyl alcohol is substituted for 1-tetradecanol, 5-(cis-9-octadecenyloxy)-2-thiophenecarboxylic acid is obtained.

EXAMPLE 5

5-Dodecyloxy-2-thiophenecarboxylic acid

When in Example 3, 1-bromododecane is substituted for 1-bromohexadecane, 5-dodecyloxy-2-thiophenecarboxaldehyde is obtained. The carboxaldehyde (5.9 g, 0.02 mole) is added to brown silver oxide formed from 7.5 g of silver nitrate and 3.5 of sodium hydroxide in 30 ml of water. The mixture is stirred vigorously overnight at room temperature, and the silver is removed and washed with water. The aqueous solution is acidified with hydrochloric acid to give 5-dodecyloxy-2-thiophenecarboxylic acid.

EXAMPLE 6

5-Tetradecyloxy-2-thiophenecarboxylic acid methyl ester

A mixture of 10.6 g of (0.031 mole) of 5-tetradecyloxy-2-thiophenecarboxylic acid, 200 ml of acetone, and 4.3 g (0.031 mole) of potassium carbonate is stirred at room temperature after which 3.9 g (0.031 mole) of dimethyl sulfate is added. The mixture is stirred with heating for about 2½ hours during which time 10 ml of methanol is added. The mixture is then diluted with 100 ml of acetone and filtered. The filtrate is evaporated to dryness to give 5-tetradecyloxy-2-thiophenecarboxylic acid methyl ester.

EXAMPLE 7

5-Tetradecyloxy-2-thiophenecarboxylic acid ethyl ester

A mixture of 10.6 g (0.031 mole) of 5-tetradecyloxy-2-thiophene carboxylic acid, 4.3 g (0.034 mole) of potassium carbonate, and dimethylformamide is stirred at room temperature after which 15.6 g (0.10 mole) of ethyl iodide is added. The mixture is heated at 50° C with stirring overnight and poured into water and extracted with the ether. The ether layer is washed with water and salt water and then dried over sodium sulfate, filtered, and the ether is distilled off to give 5-tetradecyloxy-2-thiophenecarboxylic acid ethyl ester.

aqueous potassium hydroxide 2-acetyl-5-octadecyloxythiophene is combined with 35.0 g (0.6 mole) of lithium hypochlorite. The mixture is stirred vigorously on a steam bath overnight, then allowed to cool to room temperature and extracted with ether. The aqueous extract is acidified with hydrochloric acid to precipitate 5-octadecyloxy-2-thiophenecarboxylic acid

EXAMPLE 9

5-(3,7,11,15-Tetramethylhexadecyloxy)-2-thiophenecarboxylic acid

When in Example 3, 1-bromo-3,7,11,15-tetramethylhexadecane is substituted for 1-bromohexadecane, 2-(3,7,11,15-tetramethylhexadecyloxy)thiophene is obtained. A solution of 38.1 g (0.1 mole) of 2-(3,7,11,15-tetramethylhexadecyloxy)-thiophene in 50 ml of anhydrous ether is added over a 4 hour period to 6.0 g of sodium amalgam in 100 ml of hydrous ether at reflux temperature (36°–39° C) under slight nitrogen pressure. The mixture is refluxed an additional 2 hours, then cooled to room temperature and carbonated by adding freshly crushed dry ice after which 20 ml of ethanol is added dropwise followed by the addition of 50 ml of water. The aqueous solution is separated from the ether layer, filtered and acidified with hydrochloric acid to precipitate 5-(3,7,11,15-tetramethylhexadecyloxy)-2-thiophenecarboxylic acid.

When in Example 2 an alcohol listed below is substituted for 1-tetradecanol, and a thiophenecarboxylic acid listed below is employed, the respective products are obtained.

| Ex. No. | Product | Alcohol | Thiophene carboxylic acid |
|---|---|---|---|
| 10 | 2-didecyloxy-3-thiophenecarboxylic acid | didecanol | 2-bromo-3-thiophenecarboxylic acid |
| 11 | 5-heptadecyloxy-3-thiophenecarboxylic acid | heptadecanol | 5-chloro-3-thiophenecarboxylic acid |
| 12 | 5-decylthio-2-thiophenecarboxylic acid | decanethiol | 5-nitro-2-thiophenecarboxylic acid |
| 13 | 4-hexadecylthio-2-thiophenecarboxylic acid | hexadecanethiol | 4-fluoro-2-thiophenecarboxylic acid |
| 14 | 5-(10-undecenyloxy)-2-thiophenecarboxylic acid | 10-undecen-1-ol | 5-chloro-2-thiophenecarboxylic acid |
| 15 | 5-(trans-3,7-dimethyl-2,6-octadienyloxy)-3-thiophenecarboxylic acid | trans-3,7-dimethyl-2,6-octadien-1-ol | 5-chloro-3-thiophenecarboxylic acid |
| 16 | 5-(cis-cis-9,12-octadecadienylthio)-2-thiophenecarboxylic acid | cis-cis-9,12-octadecadien-1-thiol | 5-chloro-2-thiophenecarboxylic acid |
| 17 | 5-(trans-trans-3,7,11-trimethyl-2,6-10-dodecatrienyloxy)-2-thiophenecarboxylic acid | trans-trans-3,7,11-trimethyl-2,6-10-dodecatrien-1-ol | 5-chloro-2-thiophenecarboxylic acid |
| 18 | 5-(trans-3,7-dimethyl-2,6-octadienyloxy)-2-thiophenecarboxylic acid | trans-3,7-dimethyl-2,6-octadien-1-ol | 5-chloro-2-thiophenecarboxylic acid |

EXAMPLE 8

5-Octadecyloxy-2-thiophenecarboxylic acid

When in Example 3, 1-bromooctadecane is substituted for 1-bromohexadecane, 2-octadecyloxythiophene is obtained. A mixture of 35.3 g (0.1 mole) of 2-octadecyloxythiophene and 12.3 g (0.12 mole) of acetic anhydride is cooled in an ice bath. While rapidly stirring this mixture, 1.4 g of boron trifluoride etherate is added, and the mixture is heated to 100° C with stirring for 1 hour after which it is cooled to room temperature. Ice water is added, and the mixture is extracted with chloroform. The chloroform solution is evaporated to dryness under reduce pressure to give 2-acetyl-5-octadecyloxythiophene. In 500 ml of 10%

EXAMPLE 19

5-Tetradecyloxy-2-thiophenecarboxylic acid benzyl ester

When in Example 7, benzyl chloride is substituted for ethyl iodide, 5-tetradecyloxy-2-thiophenecarboxylic acid benzyl ester is obtained.

EXAMPLE 20

5-Tetradecyloxy-2-thiophenecarboxylic acid phenethyl ester

When in Example 7, β-phenethyl chloride is substituted for ethyl iodide, 5-tetradecyloxy-2-thiophenecarboxylic acid phenethyl ester is obtained.

EXAMPLE 21

5-Tetradecyloxy-2-thiophenecarboxylic acid triester with 1,2,3-propanetriol

A mixture of 3 equivalents of 5-tetradecyloxy-2-thiophenecarboxylic acid, 1 equivalent of 1,2,3-propanetriol, and 3 equivalents of N,N'-dicyclohexylcarbodiimide in ether is stirred at room temperature for about 3 days after which the mixture is filtered. The filtrate is washed with water, dried over sodium sulfate, filtered and evaporated to dryness to give 5-tetradecyloxy-2-thiophenecarboxylic acid triester with 1,2,3-propanetriol.

EXAMPLE 22

5-Dodecyloxy-2-thiophenecarboxylic acid hexaester with inositol

When in Example 21, 6 equivalents of 5-dodecyloxy-2-thiophenecarboxylic acid is substituted for 5-tetradecyloxy-2-thiophenecarboxylic acid, 1 equivalent of inositol is substituted for 1,2,3-propanetriol, and 6 equivalents of N,N'-dicyclohexylcarbodiimide is used, 5-dodecyloxy-2-thiophenecarboxylic acid hexaester with inositol is obtained.

EXAMPLE 23

5-Tetradecyloxy-2-thiophenecarboxylic acid sodium salt

To 20.4 g (0.06 mole) of 5-tetradecyloxy-2-thiophenecarboxylic acid in 500 ml of methanol is added 5.4 g (0.10 mole) of sodium methoxide. The mixture is refluxed, and the methanol is distilled off being replaced by water. The aqueous solution is cooled, the precipitate collected, and dried to give 5-tetradecyloxy-2-thiophenecarboxylic acid sodium salt.

EXAMPLE 24

An illustrative composition for tablets is as follows:

|     |                                              | Per Tablet |
| --- | -------------------------------------------- | ---------- |
| (a) | 5-(tetradecyloxy)-2-thiophenecarboxylic acid | 100.0 mg   |
| (b) | wheat starch                                 | 15.0 mg    |
| (c) | lactose                                      | 33.5 mg    |
| (d) | magnesium stearate                           | 1.5 mg     |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 25

An illustrative composition for a parenteral injection is the following wherein the quantities are on a weight to volume basis.

|     |                                                        | Amount  |
| --- | ------------------------------------------------------ | ------- |
| (a) | 5-(tetradecyloxy)-2-thiophenecarboxylic acid sodium salt | 100.0 g |
| (b) | sodium chloride                                        | q.s.    |
| (c) | water for injection to make                            | 20 ml   |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

EXAMPLE 26

An illustrative composition for hard gelatin capsules is as follows:

|     |                                              | Amount   |
| --- | -------------------------------------------- | -------- |
| (a) | 5-(tetradecylthio)-2-thiophenecarboxylic acid | 200.0 mg |
| (b) | talc                                         | 35.0 mg  |

The composition is prepared by passing the dry powders of (a) and (b) through a fine mesh screen and mixing them well. The powder is then filled into No. 0 hard gelatin capsules at a net fill of 235 mg per capsule.

EXAMPLE 27

An illustrative composition for pills is the following:

|     |                                              | Per Pill |
| --- | -------------------------------------------- | -------- |
| (a) | 5-(tetradecylthio)-2-thiophenecarboxylic acid | 200 mg   |
| (b) | corn starch                                  | 130 mg   |
| (c) | liquid glucose                               | 20 ml    |

The pills are prepared by blending the active ingredient (a) and the corn starch then adding the liquid glucose with thorough kneading to form a plastic mass from which the pills are cut and formed.

I claim:

1. A method of reducing the lipid concentration in the blood of a patient in need thereof which comprises orally or parenterally administering to said patient a blood lipid lowering effective amount of a compound of the formula:

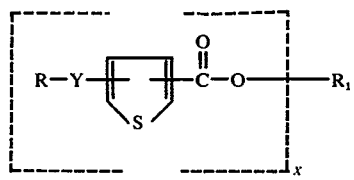

wherein Y is selected from the group consisting of oxygen and divalent sulfur; R is selected from the group consisting of a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from the group consisting of hydrogen, a straight or branched lower alkyl group of from 1 to 6 carbon atoms, benzyl, phenethyl, alkanepoly-yl containing from 3 to 6 carbon atoms and from 2 to 6 univalent bonds, and 1,2,3,4,5,6-cyclohexanehexayl; X is an integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1; or pharmaceutically acceptable salts thereof.

2. The method of claim 1 wherein the compound is of the formula:

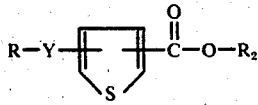

wherein R and Y have the meanings defined in claim 1; $R_2$ is selected from the group consisting of hydrogen, a straight or branched lower alkyl group of from 1 to 6 carbon atoms, benzyl and phenethyl; or pharmaceutically acceptable salts thereof.

3. The method of claim 1 wherein the compound is of the formula:

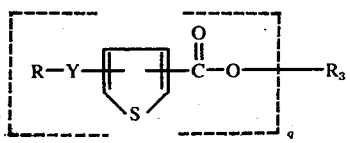

wherein R and Y have the meanings defined in claim 1; $R_3$ is selected from the group consisting of alkane-poly-yl containing from 3 to 6 carbon atoms and from 2 to 6 univalent bonds and 1,2,3,4,5,6-cyclohexanehexayl; and $q$ is an integer of from 2 to 6.

4. A method of reducing the lipid concentration in the blood of a patient in need thereof which comprises orally or parenterally administering to said patient a blood lipid lowering effective amount of a compound of the formula:

wherein Y is selected from the group consisting of oxygen and divalent sulfur; R is selected from the group consisting of a straight or branched saturated hydrocarbon chain containing from 10 to 20 carbon atoms and a straight or branched unsaturated hydrocarbon chain containing from 10 to 20 carbon atoms and from 1 to 4 double bonds; $R_2$ is selected from the group consisting of hydrogen, a straight or branched lower alkyl group of from 1 to 6 carbon atoms, benzyl and phenethyl; or pharmaceutically acceptable salts thereof.

5. The method of claim 4 wherein R represents a straight or branched saturated hydrocarbon chain containing from 10 to 20 carbon atoms.

6. The method of claim 5 wherein the compound is 5-(tetradecyloxy)-2-thiophenecarboxylic acid or pharmaceutically acceptable salts thereof.

7. The method of claim 5 wherein the compound is 5-(tetradecylthio)-2-thiophenecarboxylic acid or pharmaceutically acceptable salts thereof.

8. The method of claim 5 wherein the compound is 5-(tetradecyloxy)-2-thiophenecarboxylic acid benzyl ester.

9. The method of claim 5 wherein the compound is 5-(tetradecylthio)-2-thiophenecarboxylic acid benzyl ester.

10. The method of claim 4 wherein R is a straight or branched unsaturated hydrocarbon chain containing from 10 to 20 carbon atoms and from 1 to 4 double bonds.

11. A pharmaceutical composition in unit dosage form containing from about 50 milligrams to 1 gram of a compound of the formula:

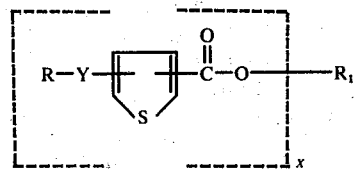

wherein Y is selected from the group consisting of oxygen and divalent sulfur; R is selected from the group consisting of a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from the group consisting of hydrogen, a straight or branched lower alkyl group of from 1 to 6 carbon atoms, benzyl, phenethyl, alkane-poly-yl containing from 3 to 6 carbon atoms and from 2 to 6 univalent bonds, and 1,2,3,4,5,6-cyclohexanehexayl; X is an integer of from 1 to 6 with the proviso that when $R_1$ is alkane-poly-yl or 1,2,3,4,5,6-cyclohexanehexayl, X is equal to from 2 to 6 and when $R_1$ is other than alkane-poly-yl or 1,2,3,4,5,6-cyclohexanehexayl, X is equal to 1; or pharmaceutically acceptable salts; and a significant amount of a pharmaceutical carrier.

12. The composition of claim 11 wherein Y is oxygen.

13. The composition of claim 11 wherein Y is sulfur.

14. The composition of claim 11 wherein the compound is of the formula:

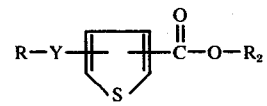

wherein Y and R have the meanings defined in claim 11; $R_2$ is selected from the group consisting of hydrogen, a straight or branched lower alkyl group of from 1 to 6 carbon atoms, benzyl and phenethyl; or pharmaceutically acceptable salts thereof.

15. The composition of claim 11 wherein the compound is of the formula:

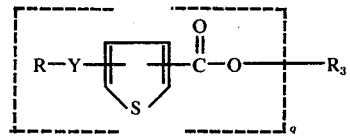

wherein Y and R have the meanings defined in claim 11; $R_3$ is selected from the group consisting of alkane-poly-yl containing from 3 to 6 carbon atoms and from 2 to 6 univalent bonds and 1,2,3,4,5,6-cyclohexanehexayl; and $q$ is an integer of from 2 to 6.

16. A pharmaceutical composition in unit dosage form containing from 50 milligrams to 1 gram of a compound of the formula:

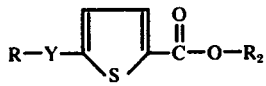

wherein Y is selected from the group consisting of oxygen and divalent sulfur; R is selected from the group consisting of a straight or branched saturated hydrocarbon chain containing from 10 to 20 carbon atoms and a straight or branched unsaturated hydrocarbon chain containing from 10 to 20 carbon atoms and from 1 to 4 double bonds; $R_2$ is selected from the group consisting of hydrogen, a straight or branched lower alkyl group of from 1 to 6 carbon atoms, benzyl and phenethyl; or pharmaceutically acceptable salts thereof; and a significant amount of a pharmaceutical carrier.

17. The composition of claim 16 wherein the compound is 5-tetradecyloxy)-2-thiophenecarboxylic acid or pharmaceutically acceptable salts thereof.

18. The composition of claim 16 wherein the compound is 5-tetradecyloxy)-2-thiophenecarboxylic acid benzyl ester.

19. The composition of claim 16 wherein the compound is 5-(tetradecylthio)-2-thiophenecarboxylic acid.

20. The composition of claim 16 wherein the compound is 5-(tetradecylthio)-2-thiophenecarboxylic acid benzyl ester.

* * * * *